United States Patent [19]

Enomoto et al.

[11] Patent Number: 4,876,024
[45] Date of Patent: Oct. 24, 1989

[54] ENZYMATIC DETERGENT ADDITIVE, A DETERGENT, AND A WASHING METHOD

[75] Inventors: Michiyo Enomoto, Tokyo, Japan; Steen Riisgaard, Ballerup, Denmark

[73] Assignee: Novo Industri A/S, Novo Alle, Denmark

[21] Appl. No.: 893,879

[22] Filed: Aug. 6, 1986

[30] Foreign Application Priority Data

Aug. 7, 1985 [DK] Denmark .............................. 3588/85

[51] Int. Cl.$^4$ ......................... C11D 3/386; C12N 9/20
[52] U.S. Cl. ............................. 252/174.12; 134/25.1; 252/DIG. 12; 435/263; 435/264; 435/198
[58] Field of Search ............... 435/263, 264; 134/25.1; 252/174.12, DIG. 12

[56] References Cited

U.S. PATENT DOCUMENTS 4,707,291 11/1987 Thom et al. .................... 252/174.12

FOREIGN PATENT DOCUMENTS 0130064 1/1985 European Pat. Off. ........ 252/174.12
1372034 10/1974 United Kingdom .
1442418 7/1976 United Kingdom ........... 252/174.12

OTHER PUBLICATIONS

"Lipases as Detergents Components", J. of App. Biochemistry, 2, (1980), pp. 218-229, by Hans Andree et al.
"Studies On Applications of Lypolytic Enzymes in Detergency II", JAOCS, vol. 62, No. 6, (June 1985).
"Washing of Oil-Stains With Lipase", presented at 16th "Symposium on Washing", held in Tokyo on Sept. 17-18, by T. Fujii, (Informal English translation herewith).

Primary Examiner—Robert A. Wax
Attorney, Agent, or Firm—Morris Fidelman; Franklin D. Wolffe

[57] ABSTRACT

A lipolytic enzymatic detergent additive, the lipase of which is from a lipase producing strain of *Pseudomonas cepacia*, detergent compositions containing such an additive and washing with the detergent compositions at temperatures below about 60° C.

11 Claims, No Drawings

ENZYMATIC DETERGENT ADDITIVE, A DETERGENT, AND A WASHING METHOD

INTRODUCTION

The art of enzymatic detergent additives has grown rapidly since its inception. For background on the art, reference is made to the article "How Enzymes Got into Detergents," Vol. 12, Developments in Industrial Microbiology, a publication of the Society for Industrial Microbiology, American Institute of Bioloical Sciences, Washington, D.C. 1971, by Claus Dambmann, Poul Holm, Villy Jensen, and Mogens Hilmer Nielsen.

The most common enzymatic detergent additive is a proteolytic additive, but lipolytic detergent additives, that portion of the art to which this invention pertains, have been suggested, e.g., in U.S. Pat. No. 4,011,116, Col. 4, line 65 to Col. 5, line 68 and Great Britain Pat. No. 1,293,613, Pg. 2, lines 6-29.

Also, a comprehensive review article directed to (commercially available) lipases as detergent additives by Hans Andree et al. is to be found in the Journal of Applied Biochemistry, 2, (1980) Pp. 218-229, entitled "Lipases as Detergents Components."

In washing processes conducted at high temperature and high alkalinity, fat in fat containing dirt is dissolved by saponification. However, low temperature washing processes (around 60° C. and below) have become common and often are preferred. At temperature below about 60° C., the lipases heretofore suggested to the art are able to dissolve only part of fat containing dirts.

Prior to the date hereof, the efficiency of lipolytic enzymatic detergent additives was measured on EMPA (Eidgenossische Materialprufungsund Versuchsanstalt, St. Gallen, Switzerland) swatches Nos. 101 (olive oil/cotton) and 102 (olive oil/wool) by adaptation of the procedure described in Great Britain Pat. No. 1,361,386 (especially Pp. 4 and 7) and U.S. Pat. No. 3,723,250 (especially Col. 15-19). Thus, the unsatisfactorily low lipolytic cleaning efficiency in low temperature washing processes exhibited by enzymes heretofore suggested for lipolytic detergent additives is evidenced by low values of the differential remittance value $\Delta R$ measured on the EMPA swatches.

Lipolytic detergent additives employing the lipase elaborated by *Fusarium oxysporum* generate substantially improved values for $\Delta R$. This lipase is superior for detergent additive purposes to all lipases previously suggested to the art. For detailed discussion of the *Fusarium oxysporum* lipase additive, reference is made to co-pending patent application, Ser. No. 623,404, filed June 22, 1984. However, it has now been discovered that considerable room exists for improvement in the actual detergency action of the *Fusarium oxysporum*, and, of course, over the detergency action of the less effective lipases.

The differential remittance value $\Delta R$ measures visual effects. If the washed garment (or swatch) looks cleaner, it must be cleaner, but exactly how much cleaner is not ascertained by the $\Delta R$ value. A more relevant measure for lipolytic cleaning efficiency is how much residual fat and fat decomposition products remain in the laundry after washing with the lipolytic detergent additive. As will be described hereinafter, such measurement is now made.

The term lipolytic detergency action is employed herein to identify the fat removal (detergency) result obtained by employing lipolytic activity during washing. Lipolytic detergency efficiency is the proportion of initially present fats removed from the laundry by lipolytic detergency action.

A need still exists for a lipolytic detergent additive which exhibits high lipolytic detergency efficiency when employed at economically reasonable lipase activities in the washing solution.

BRIEF STATEMENT OF THE INVENTION

According to the first aspect of the invention, a lipolytic detergent additive has been found which exhibits higher lipolytic detergency efficiency at economically reasonable lipase activities in the washing solution than the lipases previously known to the inventors hereof, this lipolytic detergent additive being characterized by presence therein of the lipase elaborated by a lipase producing strain of *Pseudomonas cepacia*.

Other aspects of this invention pertain to detergent compositions containing this detergent additive and to low temperature washing processes employing such detergents.

RELATION OF THE INVENTION TO THE PRIOR ART

The lipase from *Pseudomonas cepacia* is not per se novel, nor is this invention otherwise completely divorced from prior art relevant thereto. The long-sought desire of the detergent arts for an effective lipolytic detergent additive has generated a substantial body of prior art, with many lipases being suggested for pre-soak treatments of fabrics. Relatively few of these lipases are recommended as being suitable for main wash usage. Insofar as the inventors hereof are aware, the suggested lipases have not been widely employed. Lipases commercially available as of the date hereof exhibit low lipolytic detergency efficiency. Even the *Fusarium oxysporum* lipase exhibits lipolytic cleaning efficiency levels considerably lower than are obtained by practice of this invention.

It is described in Japanese Patent Application No. 135999 from 1980 that *Pseudomonas cepacia* is a lipase producer. However, it does not appear that the *Pseudomonas cepacia* lipase is described in this Japanese Patent Application as an active component in an enzymatic detergent additive.

Also, in U.S. Pat. No. 3,950,277 it is described in general terms that lipases are suited as agents for removal of oily stains from fabrics, if used together with a special group of lipase activators in a pre-soak treatment of soiled fabrics.

Aside from being exemplary of the prior art, suggestions pertaining to lipolytic treatment of soiled fabrics, this U.S. Pat. No. 3,950,277 is noteworthy for inclusion of the entire genus Pseudomonas among the many microorganism sources of suitable lipases listed in the Patent. Notwithstanding the general air of optimism to be found in U.S. Pat. No. 3,950,277, studies conducted subsequent to the date thereof have demonstrated that all of the lipases studied exhibit poor detergency results. (See Andree et al. supra.) The inventors hereof and their co-workers have ascertained that lipases truly suited to detergent usage are very rare. It so happens that the enzymatic detergent additive according to the present invention is well suited both as an ingredient in a presoaking detergent and in a main wash detergent.

Also, it is described in U.K. Pat. No. 1,372,034 that the lipase produced by means of *Pseudomonas stutzeri*

ATCC 19154 is well suited as an enzymatic detergent additive is a detergent composition comprising specified further detergent constituents. It has been found, however, that the lipolytic detergency action of the enzymatic detergent additive according to the invention is superior to the lipolytic detergency action of the enzymatic detergent additive described in the U. K. Patent. The detergent usage suitability of the *Pseudomonas cepacia* lipase is believed to be remarkable.

It is believed by the inventors hereof that failure by workers in the art to identify many lipases well suited to detergent usage is attributable to existence of characteristics required for the lipase in a lipolytic detergent additive that have no relevance to the life cycle of lipase elaborating microorganisms. Whether or not a microbial source lipase exhibits any, some, or all of the characteristics important to detergency usage is sheer happenstance. The inventors hereof and their coworkers have investigated several hundred microbial lipases with scant success. Only *Pseudomonas cepacia*, the lipase of this invention, and the lipase of *Fusarium oxysporum*, were found to be truly suitable for detergent additive usage.

THE MICROORGANISM

Some strains belonging to *Pseudomonas cepacia* are poor lipase producers. For the purposes of this invention, a lipase producing strain of *Pseudomonas cepacia* is defined as a strain which produces more than 10 LU/ml or more than 2 $NLU_{8.5}$/ml in a suitable culture medium, e.g., a medium designated LIP7 (the LU and $NLU_{8.5}$ being the lipase units defined hereinafter).

The medium LIP7 intended for shaking flasks is prepared with the following ingredients in grams per liter:

| | |
|---|---|
| PHARMAMEDIA | 20 |
| Corn steep liquor | 40 |
| Glucose | 10 |
| Soybean oil | 40 |
| Water | balance |
| pH adjusted to 7.4 before autoclaving | |
| Final pH 7.0 | |

The composition of PHARMAMEDIA is described in Traders' Guide to Fermentation Media Formulation, 1980, Traders Oil Mill Co., pp. 50-51.

In typical cultivations carried out by the inventors hereof, sterilization took place at around 130° C. for around forty minutes. A 500 ml Erlenmeyer flask with 100 ml of substrate was inoculated with cells of *Pseudomonas cepacia* from an agar slant previously inoculated with the strain to be tested for lipase production. The flasks were shaken at 200-250 rpm and at around 26° C. for four days, whereafter the lipase yield was determined.

In this Specification, several different lipases activity units have been used, i.e., the Lipase Unit (LU) described in AF 95/5-GB, and the NOVO Lipase Unit (NLU) described in AF 182/3-GB, both AF documents being available on request from NOVO INDUSTRI A/S, Novo Alle, DK-2880 Bagsvaerd, Denmark, and furthermore, a modified Novo Lipase Unit, differing only from the Novo Lipase Unit (determined at pH 7.0 or close to pH 7.0) by conduct of the activity determination at pH 8.5, this modified Novo Lipase Unit for the sake of brevity being designated $NLU_{8.5}$.

The LU activity determination method, which is quick and simple is based on hydrolysis of a short chain substrate fat, i.e., of tributyrin, but tributyrin is not representative for soiling fats that appear on textiles. The NLU method is a more elaborate activity determination method based on olive oil, a mixture of higher fatty acid triglycerides, and thus, more representative of soiling fats.

Briefly, the LU method liberates butyric acid, the amount of which is ascertained by titration with NaOH. One NOVO Lipase Unit (LU) is the amount of enzyme which, in a pH-stat and under the standard conditions stated below, liberates titratable butyric acid equivalent to 1 μmol of NaOH per minute.

| Standard Conditions | |
|---|---|
| Temperature | 30.0° C. |
| pH | 7.0 |
| Reaction time | 20 minutes |
| Substrate | tributyrin |

The NLU and $NLU_{8.5}$ methods are based on the hydrolysis of olive oil. The amount of liberated fatty acids is determined by titration with NaOH. One NOVO Lipase Unit (NLU or $NLU_{8.5}$) is the amount of enzyme which, under the standard conditions, liberates a titratable amount of fatty acid equivalent to 1 μmol of NaOH per minute.

| Standard Conditions | |
|---|---|
| Temperature | 30.0° C. |
| pH | 7.0 (NLU) or 8.5 ($NLU_{8.5}$) |
| Reaction time | 30 minutes |
| Substrate | olive oil |

THE ENZYME

As of the date hereof, only tentative and preliminary characterization data is available. Unfortunately, enzyme produced from different fermentation batches exhibited variations that generated poor reproducibility of pH and temperature stability curves. Accordingly, only ranges can be provided. The pH optimum is within the range of pH 5.75–7.0 with olive oil as substrate and ethoxylated secondary alcohol as emulsifier. The maximum pH stability is within the range of pH 6–9. The enzyme is characterized by a quite broad pH stability range being near to 100% over the range of pH 6 through 9 and by good relative activity over a wide pH range. The pH activity curve is relatively flat from pH 3–8 with at least 80% of the maximum activity obtained within the interval of pH 3–8.

Thus, this lipase exhibits excellent stability at the normally alkaline pH of (main) wash water solutions.

An important characteristic of this lipase is its excellent thermal stability. The enzyme is stable for thirty minutes at 70° C. in dilute solution at pH 8. This thermal stability generates excellent relative activity, near to 100% in the low temperature washes of below about 60° C. Thus, this lipase may be characterized as being thermally stable under low temperature washing conditions.

It is noted that the *Pseudomonas cepacia* lipase described by the aforementioned Japan Patent Application No. 135999 of 1980 and believed to be the same enzyme is reported there to have a pH optimum at pH 6.6, more than 80% relative activity over the range pH 5.5 to pH 7.5 and optimum temperature of 60° C.

It is to be understood that all lipases which are immunologically identical to the *Pseudomonas cepacia* lipase(s) are contemplated within the scope of this invention.

DETAILED PRACTICE OF THE INVENTION

In a specially preferred embodiment of the enzymatic detergent additive according to the invention, the *Pseudomonas cepacia* is selected from the strains DSM 3401 and 3333 to 3337 inclusive, especially either DSM 3335 or DSM 3401. It has been found that these strains of *Pseudomonas cepacia* give rise to a relatively high yield of lipase.

In a specially preferred embodiment of the enzymatic detergent additive according to the invention, the additive is provided as a non-dusting granulate. Granulates can be produced in several different ways. Reference can be made to Great Britain Pat. No. 1,362,365 for details on the production of enzyme containing granulates used as detergent additives by means of an apparatus comprising an extruder and a spheronizer (sold as MARUMERIZER ®), and to U.S. Pat. No. 4,106,991 for details on the production of enzyme containing granulates used as detergent additives by means of a drum granulator.

In a specially preferred embodiment of the enzymatic detergent additive according to the invention, the additive is provided as a liquid.

In a specially preferred embodiment of the enzymatic detergent additive according to the invention, the additive is provided as a liquid with an enzyme stabilizer. The stabilizer may be propylene glycol or other agents known in the art to stabilize enzyme solutions. Liquid detergents are of growing popularity due to the ease of application.

In a specially preferred embodiment of the enzymatic detergent additive according to the invention, the lipase activity is above about 2,500 NLU/g of additive. In this manner, a convenient lipase activity is generated in the washing solution when the detergent additive is present in the detergent composition in an amount of 0.05 to 10.0 preferably 0.1–2.0 g/100 g of detergent composition, for when the detergent composition is added to the washing solution in an amount of 1–20 g of detergent composition per liter of washing solution.

A convenient lipase activity generated in the washing solution is, typically, between 1,000 and 5,000 NLU/l of washing solution.

In a specially preferred embodiment of lipolytic enzymatic detergent additive according to the invention, the additive contains a proteolytic enzyme besides the lipase. Surprisingly, it has been found that the proteolytic enzyme does not break down the protein of the lipase, neither in the additive, nor in the detergent composition, nor in the washing solution. Thus, the proteolytic and the lipolytic enzymes are compatible detergent additives, and it has been found that such a combined lipolytic and proteolytic detergent additive has a very high cleansing efficiency. The *Bacillus licheniformis*, proteolytic enzyme, ALCALASE ® from NOVO INDUSTRI A/S, for example, can be used with superior results in a combined lipolytic and proteolytic enzymatic detergent additive. The mixed enzymatic additive can be prepared either by mixing a previously prepared granulate of proteinase with a previously prepared granulate of lipase, or by mixing a concentrate of proteinase with a concentrate of lipase and then introducing this mixture into a granulating device, together with the usual granulating aids.

In a specially preferred embodiment of lipolytic and proteolytic enzymatic detergent additive according to the invention, the proteolytic activity therein is between about 0.5 and about 3.0 Anson Units/g of additive. At such concentrations, a convenient proteolytic activity is generated in the washing solution when the detergent additive is added to the detergent in an amount of 0.2–2.0 g/100 g of detergent composition, and when the detergent composition is added to the washing solution in an amount of 1–20 of washing solution.

The second aspect of the invention comprises a detergent composition with a lipolytic enzymatic detergent additive as described above incorporated in the detergent composition.

Preferably, the detergent composition contains the lipolytic enzymatic detergent additive in an amount of between 0.01 and 50.0% w/w, preferably between 0.1 and 2% w/w. At such concentrations, a reasonable balance between enzyme action and the action of the other detergent ingredients is generated.

The third aspect of the invention comprises a washing process in which the detergent used is a detergent composition containing a lipolytic enzymatic detergent additive as described above, and in which the washing pH is between 7 and 11, and the washing temperature is below about 60° C. In a specially preferred embodiment of the invention, the washing solution contains the detergent composition in an amount of between 1 and 20 g/l of washing solution. At such concentrations, a convenient enzyme activity is generated in the washing solution, typically between 1,000 and 5,000 NLU/l of washing solution. Under these circumstances, very high lipolytic detergency efficiency is obtained for usual washing times, which, for example, may be about twenty minutes.

For further understanding of this invention and to illustrate practice thereof, the following Examples are presented. Examples 1–7 are Production Examples and Examples 8–13 are Washing Examples.

EXAMPLE 1

A culture of *Pseudomonas cepacia* DSM 3401 on an agar slant was transferred to five 500 ml shaking flasks, each with 100 ml of Bouillon-3 medium, and shaken at 30° C. for one day (200 rpm, amplitude 2.5 cm).

The composition of Bouillon-3 was as follows:

| Constituent | Concentration, g/l |
| --- | --- |
| Peptone | 6 |
| Trypsin digested casein | 4 |
| Yeast Extract | 3 |
| Meat Extract | 1.5 |
| Glucose | 1 |
| Water | Balance |

The medium was autoclaved at 121° C. for forty minutes. The culture broth of these Bouillon-3 shake flasks were used as a seed culture for inoculating two hundred 500 ml shake flasks, each with 200 ml PL-1 medium.

The composition of the PL-1 medium was as follows:

| Constituent | Concentration, g/l |
| --- | --- |
| Peptone | 10 |
| Tween-80 | 12 |
| MgSO$_4$.7H$_2$ | 2 |
| CaCl$_2$.2H$_2$O | 0.1 |
| Water | Balance |
| pH before autoclaving | 6.0 |

The medium was autoclaved at 121° C. for forty minutes.

Each PL-1 shake flask was inoculated with 0.5-2 ml of Bouillon-3 culture broth, and shaken with 200 rpm (amplitude 2.5 cm) at 30° C. for five days. The culture broth from the shake flasks were pooled at harvest, totaling 39.5 liters with an enzyme yield of 53 LU/ml.

The culture broth was centrifuged for 35 minutes at 4100 g by means of a Beckman Model J-6 centrifuge. The supernatant was concentrated by ultrafiltration (washed with approximately one volume of water) to 1.4 liters by a Pellicon ultrafiltration apparatus from Millipore with a 10,000 MW cutoff filter sheet. The concentrate was freeze-dried and the yield was 56.2 g of powder with an enzyme activity of 21,500 LU/g.

EXAMPLES 2-6

In the following Production Examples 2-6, 100 ml of medium in a 500 ml shake flask was inoculated with cultues originating from the specified strains of *Pseudomonas cepacia* on agar slants incubated at around 30° C. for about three days. The medium in Examples 2-6 was the LIP7 already described herein. The shake flasks were incubated for four days at around 26° C. and at 200-250 rpm. The lipase activity of the broth (NLU$_{8.5}$/ml) was measured, and the broth was directly used as lipase source in the later described Washing Example.

Examples 7 and 13 are comparison Examples which employed *Fusarium oxysporum* lipase, obtained as described in Example 23 of Ser. No. 623,404, filed June 22, 1984, and in the corresponding European Patent Application with Publication No. 0,130,064.

The results are tabulated below.

| Production example No. | Strain DSM No. | Lipase activity of broth NLU$_{8.5}$/ml | Lipase activity of powder NLU$_{8.5}$/g | Corresponding washing example No. |
| --- | --- | --- | --- | --- |
| 2 | 3333 | 13.0 | | 8 |
| 3 | 3334 | 7.7 | | 9 |
| 4 | 3337 | 7.1 | | 10 |
| 5 | 3335 | 10.4 | | 11 |
| 6 | 3336 | 4.1 | | 12 |
| 7 | — | — | 28300 | 13 |

The washing examples 8-13 were carried out as follows.

Cotton swatches (obtained from the Japan Oil Chemists' Society and designated No. 6) measuring 7.5×5.0 cm and weighing 0.52 g were treated with 0.5 ml of 3% beef tallow solution in chloroform on each side.

The swatches were cut into 8 pieces of approximately the same size. These 8 pieces were transferred to a small reaction vessel containing 10 ml of enzyme solution with specified lipase activity (NLU$_{8.5}$/ml) and with pH 8.5, controlled by means of an approximately 0.2M buffer of TRIS/HCl (Tris=2-amino-2-hydroxymethyl-1,3-propanediol). The reaction mixture was incubated for 1 hour at 40° C. with shaking. Then 40 μl of 10% LAS in 0.2M borate buffer (pH 10) was added to the reaction mixture. Now the reaction mixture was incubated for 15 minutes at 40° C. with shaking. 100 μl of the washing solution was withdrawn for the assay of free fatty acids.

The assay of free fatty acids was carried out colorimetrically in accordance with the method described in the brochure Code 279-75401 Nefa C-test Wako obtainable from Wako Chemicals, GmbH, Nissan Strasse 2-4040, Neussl, West Germany, except that a 100 μl sample was used instead of a 50 μl sample, reagent samples A and B were 0.5 and 1 ml instead of 1 and 2 ml respectively and that the assay was carried out at 40° C. instead of 37° C. A cuvette with a path length of 1 cm was used for the spectrophotometric measurement. The spectrophotometric reading at 550 nm $A_1$ for the washing solution being corrected for the spectrophotometric reading at 550 nm $A_0$ for a blank (a 100 μl enzyme sample taken out from the reaction vessel before incubation) is the Δ A value ($\Delta A = A_1 - A_0$) representing the amount of free fatty acids in the washing solution liberated from the swatches. Thus, Δ A is an indication of the lipolytic washing efficiency.

Below tabulated are the results from Washing Examples 8-12. Example 13 is the comparative Washing Example performed with *Fusarium oxysporum* lipase.

| Example No. | Lipase originating from example No. | Lipase activity in washing solution, NLU$_{8.5}$/ml | ΔA |
| --- | --- | --- | --- |
| 8 | 2 | 2.6 | 0.48 |
| 9 | 3 | 1.6 | 0.53 |
| 10 | 4 | 2.8 | 0.41 |
| 11 | 5 | 2.1 | 0.59 |
| 12 | 6 | 2.1 | 0.56 |
| 13 | 7 | 2.8 | 0.21 |

The measurement Δ A can be related to fat removal; 1 Δ A corresponds to 8% fat removal. Thus, all Δ A test results represent hydrolysis of very low proportions of fat. It should, however, be appreciated that a very large proportion of tallow was incorporated in the swatches (<5% w/w) and no detergent was present in the reaction mixture. The Δ A measurement ascertains the unaided capability of a lipase to remove adsorbed fat through hydrolysis. The data tabulated above demonstrates that the enzymatic detergent additive according to the present invention is superior to the *Fusarium oxysporum* lipase (which was the best detergent purposes lipase known heretofore). Substantially more free fatty acid was released from the swatches in the washing solution at comparable values of lipase activity expressed as NLU$_{8.5}$/ml. Moreover, measurements of cleaning capability through differential remittance values, Δ R, also have demonstrated the superiority of the *Pseudomonas cepacia* lipase.

We claim:

1. A lipolytic enzymatic detergent additive in the form of a non-dusting granulate or a stabilized liquid, the active enzyme component of which is a lipase produced by a lipase producing strain of *Pseudomonas cepacia* said lipase being characterized by a pH activity optimum within the pH range of pH 5.75-7.0 and by being thermally stable at 60° C.

2. An enzymatic detergent additive according to claim 1 wherein the lipase producing strain of *Pseudomonas cepacia* is selected from the group consisting of DSM 3333 to 3337 inclusive and 3401.

3. An enzymatic detergent additive according to claim 1 wherein the additive is in the form of a non-dusting granulate.

4. An enzymatic detergent additive according to claim 1 wherein the additive is a liquid, the liquid containing therein an enzyme stabilizer.

5. An enzymatic detergent additive according to claim 1 wherein the lipase activity therein is more than about 2,500 NLU/g of additive.

6. An enzymatic detergent additive according to claim 1 wherein the additive further comprises a proteolytic enzyme.

7. An enzymatic detergent additive according to claim 6 wherein the proteolytic activity therein is between about 0.5 and about 3.0 Anson Units/g of additive.

8. A detergent composition containing therein a lipolytic enzymatic additive, the enzyme component of which is a lipase produced by a lipase producing strain of *Pseudomonas cepacia*, said lipase being characterized by a pH activity optimum within the pH range of pH 5.75–7.0 and by being thermally stable at 60° C.

9. A detergent according to claim 8 wherein the detergent composition contains therein the lipolytic enzymatic detergent additive in an amount of between 0.1 and 2.0% w/w.

10. A washing process which comprises washing at a temperature below about 60° C. at a pH between 7 and 11 with a detergent composition containing therein a lipolytic enzyme additive, the enzyme component of which is a lipase produced by a lipase producing strain of *Pseudomonas cepacia*, said lipase being characterized by a pH activity optimum within the pH range of pH 5.75–7.0 and by being thermally stable at 60° C.

11. A washing process according to claim 10 wherein the solution employed for washing contains the detergent in an amount of between 1 and 20 g per liter of washing solution.

* * * * *